(12) United States Patent
Ferguson

(10) Patent No.: US 7,767,936 B2
(45) Date of Patent: *Aug. 3, 2010

(54) FUNCTIONAL THERAPEUTIC HEATER

(75) Inventor: Patrick Ferguson, North Shields (GB)

(73) Assignee: Nel Technologies Limited, Throckley (GB)

( * ) Notice: Subject to any disclaimer, the term of this patent is extended or adjusted under 35 U.S.C. 154(b) by 995 days.

This patent is subject to a terminal disclaimer.

(21) Appl. No.: 10/558,851

(22) PCT Filed: Jun. 2, 2004

(86) PCT No.: PCT/GB2004/002346

§ 371 (c)(1),
(2), (4) Date: Aug. 24, 2006

(87) PCT Pub. No.: WO2004/107816

PCT Pub. Date: Dec. 9, 2004

(65) Prior Publication Data

US 2007/0108190 A1    May 17, 2007

(30) Foreign Application Priority Data

Jun. 2, 2003    (GB) ................................. 0312552.3

(51) Int. Cl.
*H05B 1/00*    (2006.01)
(52) U.S. Cl. ........................ 219/219; 219/549; 219/528; 219/211; 338/208
(58) Field of Classification Search ................. 219/219, 219/211, 548, 549, 527; 338/208
See application file for complete search history.

(56) References Cited

U.S. PATENT DOCUMENTS 2,717,949 A * 9/1955 Challenner .................. 219/618

(Continued)

FOREIGN PATENT DOCUMENTS

DE    3210097    9/1983

(Continued)

OTHER PUBLICATIONS

Adeyeye, C. M. and Price, J. C., "Development and Evaluation of Sustained Release Ibuprofen-Wax Microspheres: I. Effect of Formulation Variables on Physical Characteristics", Pharmaceutical Research, vol. 8, No. 11, pp. 1377-1383 (1991).

(Continued)

*Primary Examiner*—Thor S Campbell
*Assistant Examiner*—Vinod D Patel
(74) *Attorney, Agent, or Firm*—Barlow, Josephs & Holmes, Ltd.

(57) ABSTRACT

A breathable electrical heater element for a topical application device such as a wound dressing or a therapeutic heating pad is disclosed. The heater element is formed by photochemically etching a track pattern onto a porous metallised fabric (e.g. nickel coated woven polyester). The heater element has a skin or wound contact layer laminated to the front face of the heater element. An adhesive layer is laminated to the back face of the heater element. The adhesive layer forms an overhang to provide an adhesive border around the wound contact layer to adhere the device to the skin of a patient. Therapeutically active drugs (optionally microencapsulated) may be incorporated into the skin or wound contact layer. Operation of the heater element causes the skin or wound contact layer to release the active drugs to the skin or wound of the patient. Appropriate control of the temperature of the heater element allows control of the release of the active drugs.

10 Claims, 1 Drawing Sheet

U.S. PATENT DOCUMENTS

| | | | |
|---|---|---|---|
| 3,296,415 A | | 1/1967 | Eisler |
| 3,660,088 A | | 5/1972 | Lundsager |
| 3,767,398 A | | 10/1973 | Morgan |
| 4,066,078 A | * | 1/1978 | Berg .................... 600/391 |
| 4,201,825 A | | 5/1980 | Ebneth |
| 4,257,176 A | | 3/1981 | Hartung et al. |
| 4,508,776 A | * | 4/1985 | Smith .................... 442/230 |
| 4,565,745 A | | 1/1986 | Kaminskas |
| 4,743,740 A | | 5/1988 | Adee |
| 4,798,933 A | | 1/1989 | Annovi |
| 4,948,951 A | | 8/1990 | Balzano |
| 5,041,717 A | | 8/1991 | Shay, III et al. |
| 5,352,862 A | | 10/1994 | Barr |
| 5,534,021 A | | 7/1996 | Dvoretzky et al. |
| 5,580,573 A | | 12/1996 | Kydonieus et al. |
| 5,648,003 A | | 7/1997 | Liang et al. |
| 5,829,171 A | | 11/1998 | Weber et al. |
| 6,172,344 B1 | | 1/2001 | Gordon et al. |
| 6,227,458 B1 | | 5/2001 | Dever et al. |
| 6,229,123 B1 | | 5/2001 | Kochman et al. |
| 6,294,313 B1 | | 9/2001 | Kobayashi et al. |
| 6,309,986 B1 | | 10/2001 | Flashinski et al. |
| 6,423,018 B1 | | 7/2002 | Augustine |
| 6,436,063 B1 | | 8/2002 | Augustine et al. |
| 6,501,055 B2 | | 12/2002 | Rock et al. |
| 6,551,560 B1 | | 4/2003 | Flashinski et al. |
| 6,613,350 B1 | | 9/2003 | Zhang et al. |
| 7,115,844 B2 | | 10/2006 | Ferguson |
| 2001/0002669 A1 | | 6/2001 | Kochman et al. |
| 2003/0124167 A1 | | 7/2003 | Thies |
| 2007/0187392 A1 | | 8/2007 | Ferguson |
| 2007/0210051 A1 | | 9/2007 | Ferguson |

FOREIGN PATENT DOCUMENTS

| | | |
|---|---|---|
| GB | 2092868 A | 8/1982 |
| GB | 2175849 A | 12/1986 |
| GB | 2205496 A | 12/1988 |
| GB | 2336514 A | 10/1999 |
| GB | 2383197 A | 6/2003 |
| JP | 60047686 A | 3/1986 |
| JP | 03037021 | 2/1991 |
| JP | 04002079 | 1/1992 |
| WO | 8810058 A1 | 12/1988 |
| WO | 0101855 A1 | 1/2001 |
| WO | 0124580 A1 | 4/2001 |
| WO | 03039417 A2 | 5/2003 |
| WO | 03053101 A1 | 6/2003 |

OTHER PUBLICATIONS

Adeyeye, C. M. and Price, J. C., "Development and Evaluation of Sustained Release Ibuprofen-Wax Microspheres: II. In vitro Dissolution Studies", Pharmaceutical Research vol. 11, No. 4, pp. 575-579 (1994).

Adeyeye, C. M. and Price, J. C., "Chemical, dissolution stability and microscopic evaluation of suspensions of ibuprofen-wax microspheres", Journal of Microencapsulation, vol. 14, pp. 357-377 (1997).

US 6,290,977, 09/2001, Friars et al. (withdrawn)

* cited by examiner

FUNCTIONAL THERAPEUTIC HEATER

BACKGROUND TO THE INVENTION

1. Field of the Invention

The invention relates to a therapeutic heater element. In preferred embodiments, the invention relates to a breathable, porous, flexible fabric heater that is incorporated into heating pads for therapy or pain relief and/or wound dressings and a thermally activated drug and chemical delivery system.

2. Related Art

The use of direct heating for the therapeutic treatment of joint and muscular pain in humans is a known practice and is claimed to bring significant relief to patients (U.S. Pat. No. 5,534,021). The application of heat directly to wound sites has also been reported to contribute to improved wound management and healing (WO03/039417).

Known thermal therapies have relied on the use of:
a) IR metal radiators (which can be applied to the patient in the form of a wrap and which may be disposed of after use);
b) electrical infra-red heating devices;
c) carbonised fibre heater elements; and
d) exothermic materials.

Furthermore, it is also known to deliver drugs through the skin of a patient using a heated contact pad, as disclosed in U.S. Pat. No. 6,613,350.

SUMMARY OF THE INVENTION

The present inventor has realised that known electrical heating devices have some drawbacks and limitations that limit their potential use in therapeutic applications. These include high cost, lack of breathability, brittleness, inflexibility, restricted portability and a lack of disposability. Accordingly, the present invention has been made in order to address these drawbacks and limitations, and preferably to reduce, ameliorate or even overcome them.

The present inventor has realised that there is a need for a cost-effective, disposable electrical heating system. Such a heating system may find use in deep-heat therapeutic muscular and joint pain treatment and/or in wound-care, where thermal regulation of the wound site is considered beneficial. In addition, the heating system may find use in utilising thermal regulation to deliver drugs and/or other medicinal chemicals to the wound site. It may also find use in assisting in vaso-dilation prior to cannulation, for example. This is of particular importance in paediatric medicine.

Accordingly, in a first aspect, the present invention provides a therapeutic heater element formed from flexible metallised fabric, for topical application for treatment.

Typically, the heater element is formed by photochemical etching of metallised fabric.

Details of the construction, manufacture and heating performance of a suitable flexible, porous etched metallised fabric heater are described in WO03/053101, the content of which is incorporated by reference in its entirety. WO03/053101 claims priority from UK Patent Application No. 0228999.9, filed 14 Dec. 2001.

Preferably, the heater element has termination pads. These are at the end of the etched track and allow connection of the heater element to a battery/control system.

It is contemplated that the present invention is of use both in a therapeutic heat-treatment topical application device (e.g. a pad) and in a wound topical application device (e.g. dressing). Both of these devices are therefore preferred aspects of the invention.

Preferably, the heater element is porous. This allows the pad or dressing to be breathable.

An advantage of using an electrical heating system rather than a chemical heating system (e.g. using the heat generated by an exothermic reaction) is that the temperature of the heating system can be regulated and controlled either manually by the patient or medical practitioner or automatically by suitable control circuitry. Preferably, the topical application for treatment includes a power source (such as a battery) for connection to the heater element. Optionally, it may also include control circuitry for controlling the temperature of the application.

Preferably, the heater element is held within either a partially or fully integrated textile or nonwoven fabric laminate. The device may be designed to be wearable, conformable and discrete in use. Preferably, the device is capable of controlling the microclimate between the heater and the body.

Preferably, the device has at least one therapeutic agent for delivery to a subject. The delivery of the therapeutic agent or agents to the subject may be assisted by operation of the heater element to generate heat. For example, the device may be a drug-delivery system for wound management for enabling the administration of therapeutic preparations to a patient (e.g. growth factors and ointments). The therapeutic agent may be a pain-relieving formulation (e.g. ibuprofen or similar) or it may be a vaso-dilation formulation (e.g. EMLA or similar).

In a preferred approach, the therapeutic agent or agents of interest are microencapsulated in microcapsules. Suitable microcapsules are those that melt at a particular initiation temperature. Alternative microcapsules are those that allow diffusion of the active chemicals through their walls to effect a slow release mechanism from the device. By appropriate temperature control, the heater element may then be used to initiate the delivery of such active chemicals or agents. It will be understood that by the encapsulation of various active agents and the use of microcapsules having different thermal characteristics, the timing of the delivery of each agent can be controlled as required.

In a preferred embodiment, an etched breathable metallised fabric heating element is laminated or otherwise attached to a nonwoven or textile fabric, which forms part of a skin contact pad or wound dressing. The heater element may be a component in a bilaminate or multilaminate structure as required. The porous heater element with an appropriate track pattern may be encapsulated in a suitable continuous polymer to produce a breathable, water-proof, flexible, thin heater element, which by the use of a suitable connector to a portable battery can be powered to deliver significant thermal energy to the wearer. Preferably, the thickness of the heater element is less than 1 mm (e.g. <1.0 mm).

During manufacture of the heater element, it is possible to select the width, length and shape of the etched-track pattern. The selection can be varied widely to optimise the heater element performance in use or to provide differential heating across the heater element in use.

Preferably, the heater element is capable of being controlled to regulate the rate of heating and/or the maximum heat output. Regulation can be achieved either manually by the wearer via a suitable control device or automatically by the heater system itself (which may be pre-programmed as necessary).

The heater element may therefore be controllable to provide a time-dependent heating profile (e.g. a gradual increase in temperature or a step-wise increase in temperature) during use. This is of particular use where, more than one active agent is contained in the topical application. Each active agent may be selected in order to be released at a particular temperature. Thus, the control of the temperature of the device allows the control, of the release of the active drug to the subject.

The preferred thin and flexible characteristics of the heater element minimise stiffening of the pad or dressing and ensure it is able to conform to the shape of different sites and extremities on the body where heat treatment is needed.

Preferred features of a therapeutic heating pad according to an embodiment of the invention will now be set out.

A heating pad preferably has a skin contact layer selected from nonwoven and/or other textile structures that are known skin contact layer materials (e.g. hydroentangled, thermal bonded or needlepunched nonwovens may be used as well as knitted, woven, mesh fabrics or continuous or perforated films). The pad may be breathable and may also be absorbent due to the hydrophilic nature of a polymer composition (as required).

The heater element may be laminated to the skin contact layer or to a backing layer using a thermoplastic web material. Such materials are typically fibrous and have a high degree of open porosity. Typical thermoplastic webs soften when heated (e.g. to around 130° C.). Pressure may be applied to speed up the softening of the material. Typically, the thermoplastic web material is located between the heater element and the skin contact layer. This arrangement is then heated and pressed so that the thermoplastic web is softened and deformed to adhere the heater element to the skin contact layer to form a laminate.

Preferably, the flexible, porous heater element is laminated or otherwise attached to the back of the contact layer in such a way that heat energy can be transferred through the contact layer by the mechanisms of conduction and/or convection. A retaining layer or backing layer (having an approved skin contact adhesive) may be applied over the laminate to fix its position on the patient. Alternatively, the adhesive layer may be laminated to the reverse side of the heater element to form a fully integrated tri-laminate structure.

Suitable electrical connection for powering the heater element may be provided at the extremity of the pad.

Preferably, the connection is capable of disconnection from the battery after use.

Preferably, the heating pad is thin and conformable and when fixed in place by a suitable adhesive retaining layer can be operated and worn by the patient without restricting their normal activities. Differential heating of the patient over the area of the heater element can be achieved by selecting an appropriate element track pattern during manufacture and/or by suitable adjustment of the temperature control provided to the heater element.

Preferably, the pad includes means for administering therapeutic drugs or chemicals to the patient through the skin contact pad by appropriate regulation of the temperature of the heater element to initiate the release of encapsulated or non-encapsulated active chemicals.

In a preferred embodiment a liquid permeable nonwoven skin contact pad or perforated film is pre-impregnated or coated with microencapsulated therapeutic drugs or chemicals. Preferably, the delivery of these functional components is achieved by diffusion through the walls of the microcapsules or by melting of the microcapsules (induced by the heater element), which releases the encapsulated components. By applying different microencapsulated drugs or chemicals in microcapsules having different thermal properties it is possible to deliver the active drugs or chemicals at different intervals by adjusting the heater element temperature.

Suitable materials for encapsulating suitable agents include lipids such as wax, paraffin, tristearin, stearic acid, monoglycerides, diglycerides, beeswax, oils, fats and hardened oils.

In the case where the active agent is ibuprofen, it is preferred the agent is encapsulated within wax microspheres, according to known encapsulation techniques.

In the case where the active agent is EMLA (a mixture of active agents) it may be preferred not to microencapsulate the agent.

Preferred features of a wound dressing according to an embodiment of the invention will now be set out.

The potential benefits of heating a wound site are set out in U.S. Pat. No. 6,423,018 and U.S. Pat. No. 6,436,063. These include increased cutaneous and subcutaneous blood flow and increased immune system functions both humoral and cell mediated, including increased migration of white blood cells and fibroblasts to the site.

The microclimate of the wound-site (including temperature and moisture vapour), are important in the process of wound healing and can be influenced by the type of wound dressing used (e.g. occlusive or non-occlusive). Whilst a moist wound site has been shown to be beneficial for healing, excessive wetting out of the wound and the surrounding area can cause tissue maceration and an increased probability of infection. It is anticipated that the ability to control the temperature of the wound site may also provide a means of regulating the relative humidity and control the potential for condensation, which can lead to maceration. Wound site microclimate control is preferably achieved by the present invention.

It is preferred that, in use, the dressing provides a means for regulating the temperature of the wound site to maintain a mean temperature (e.g. normal skin temperature). The availability of a temperature/concentration gradient across the wound contact layer also provides a useful means for the delivery of drugs and other chemicals to the wound site from within the dressing.

Preferably, the breathable fabric heater element is incorporated into a standard disposable wound dressing architecture, which in simple form consists of a wound contact layer (e.g. knitted or woven gauzes, nonwoven fabrics or films) to which a porous flexible heater element is attached to the reverse side. More preferably, the fabric heater element is incorporated in such a way that there is substantially no possibility of body fluids coming into contact with its surface, which might otherwise induce an immunological response depending on the surface chemistry of the element.

Preferred embodiments of the invention include composite and island-dressing structures. Typically, these have a wound contact layer (e.g. a low adherent film) attached to an absorbent or superabsorbent core. In turn this may be covered by a moisture vapour permeable retaining layer, which may have an approved skin-contact adhesive around its inner surface to allow its fixation to the patient. In such composite dressings, the flexible heater element is preferably incorporated above the absorbent core rather than immediately above the wound contact layer. Alternatively, a breathable film may be used to separate the absorbent core from the heater element. This may be preferable when high levels of wound exudates are produced (e.g. pressure sores).

The flexible metallised fabric may be shaped so as to provide terminals for electrical connection of tracks formed on the fabric at an elongate flexible tail portion of the fabric. In this way, the heat-generating tracks may be connected to a suitable power supply via the terminals at the tail portion.

This avoids the need for conventional wires to be trailed through the dressing or pad from the power supply to the fabric.

Preferably, drugs and/or other functional chemicals are deliverable to the wound site via the wound contact layer. Typically, the delivery of these agents is triggered by the heat energy produced by the fabric heater element. In one embodiment, drugs and/or chemicals such as antimicrobials, ointments, growth factors, steroids and other therapeutic preparations are encapsulated in microcapsules, and are delivered by diffusion through the wall or by thermal degradation or melting of the microcapsule. The microencapsulated drugs and chemicals may be applied to the dressing by any known methods e.g. by coating or saturation impregnation.

The microcapsules may be applied directly to the wound contact layer or to other layers in the dressing depending on its particular design. In a preferred embodiment, the heater element is used to initiate complete or partial melting (fusion) of the microcapsule wall to release the active components to the wound site. Using this temperature-induced approach to drug delivery, it is therefore possible to administer various topical treatments by applying different microencapsulated drugs and chemicals on to the dressing and by using microcapsules having different thermal properties.

DESCRIPTION OF THE PREFERRED EMBODIMENTS

Figure 1:
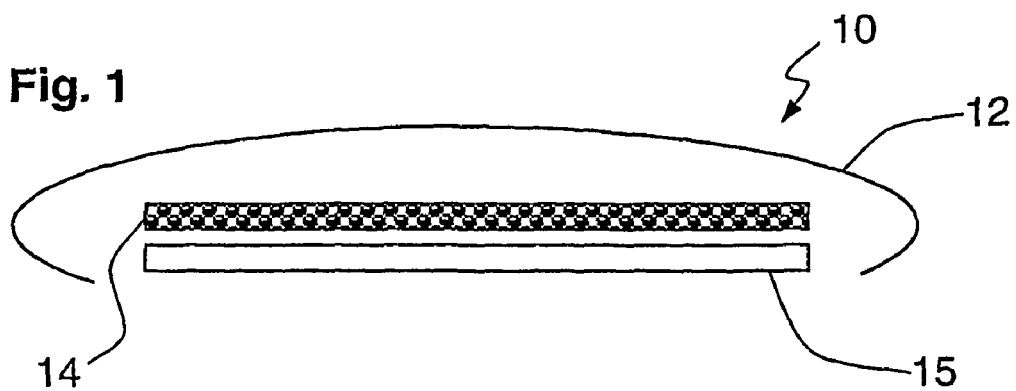
FIG. 1 shows a schematic sectional view of a thermal treatment pad according to an embodiment of the invention.

FIG. 1 shows a schematic view of a thermal treatment pad 10 according to an embodiment of the invention. Skin contact layer 15 has disposed above it a flexible, breathable metallised fabric heater element 14 that is described in more detail below. The pad is held together and affixed to a patient's skin by adhesive layer 12.

Figure 2:
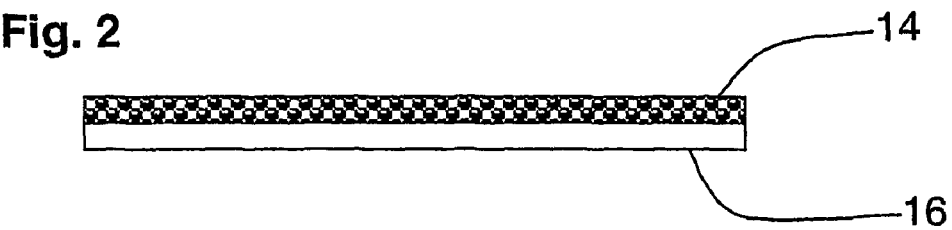
FIG. 2 shows a schematic sectional view of a laminated structure according to an embodiment of the invention.

FIG. 2 shows a schematic view of a laminated structure including a wound contact layer 16 laminated to heater element 14. The wound contact layer is, for example, a woven gauze material of low adherence that is known in the art of wound dressings. Alternative materials for the wound contact layer include a low adherence film, mesh or nonwoven fabric (including absorbent and superabsorbent compositions).

Figure 3:
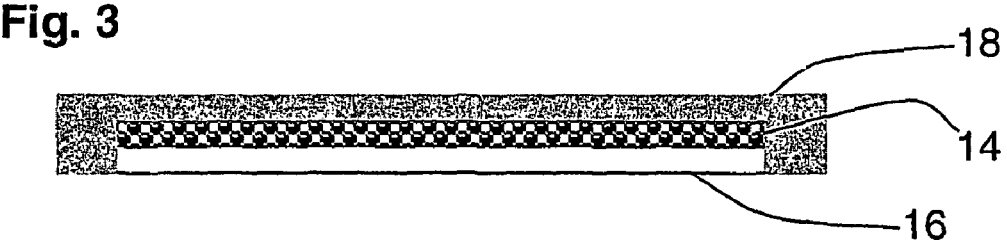
FIG. 3 shows a schematic sectional view of a wound dressing according to an embodiment of the invention.

FIG. 3 shows the laminated structure of FIG. 2 incorporated into an island wound dressing. Adhesive retaining layer 18 is laminated to the back surface of the heater element 14 and extends forwardly to be substantially flush with the front surface of wound contact layer 16. When applied over a wound of a patient, the adhesive retaining layer 18 adheres to the patient's skin surrounding the wound to retain the dressing with respect to the wound and the patient.

Figure 4:
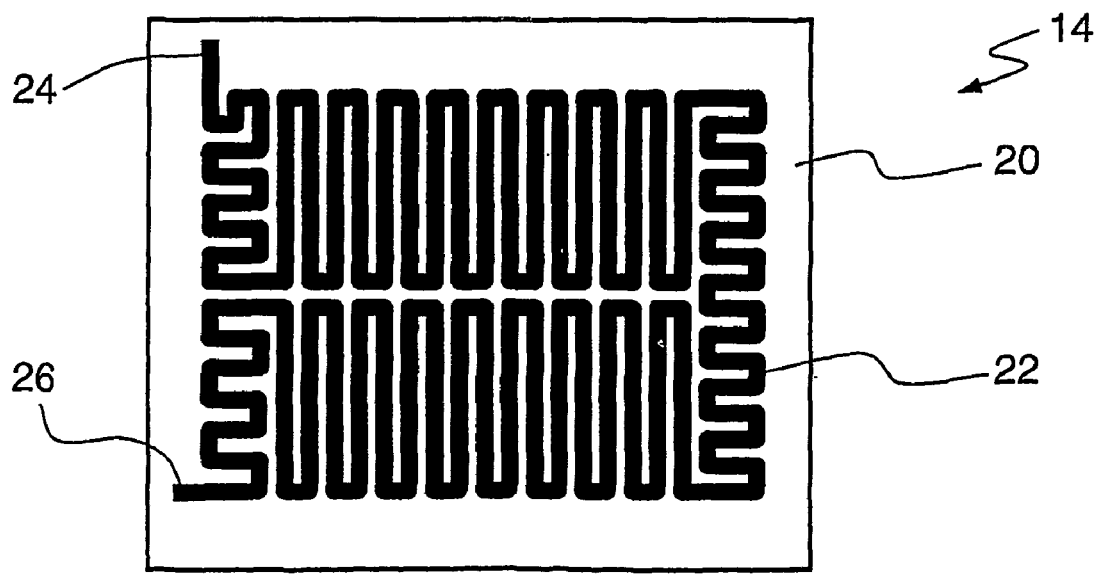
FIG. 4 shows a schematic plan view of a heater element for use in the wound dressing of FIG. 3.

FIG. 4 shows a plan view of the heater element 14 used in the wound dressing of FIG. 3. A similar heater element is also suitable for use in the thermal treatment pad 10 of FIG. 1. In FIG. 4, a metallic track 22 is etched from a piece of porous metallised fabric (typically nickel-coated woven polyester) to leave track 22 and etched fabric 20. The pattern of the track is such that terminal connection points 24, 26 are formed, for connection to a power source such as a battery and suitable control circuitry to control/limit the heat output of the heater element 14 in use.

The heater element is formed by taking a nickel coated polyester woven fabric and cutting it to the shape required for the thermal treatment pad or wound dressing after the formation of the heater track pattern by photochemical etching, as described below. A suitable material is the commercially available metallised fabric Metalester (Registered Trade Mark), a woven electroless nickel plated polyester mesh. Such fabrics are available with a variety of thread thicknesses, thread spacings, type of weave and weight of nickel. Threads may typically have a diameter within the range 24 to 600 micrometers (microns), a thread count of between 4 and 737 per cm, and a metal coating of varying weight per square metre.

Suitable fabrics may be coated with a continuous layer of metal after manufacture, for example by sputtering, by chemical reduction or by electro-deposition, which results in total encapsulation of all the threads of the mesh in metal. In an alternative mesh, the individual warp and weft threads may be metallised prior to fabric production, for example by sputtering, by chemical reduction or by electro-deposition.

After selecting the desired metallised fabric, the desired track pattern is photochemically etched from the fabric. This is done by first designing and generating a suitable phototool, in a way well known to the skilled person. Next, the fabric is mounted onto a hinged frame of brown styrene board, so that the otherwise flimsy fabric can be more readily handled. The fabric is then cleaned with a commercial surface cleaning agent to assist in the adhesion of the photoresist. Then, the photoresist is applied, typically by dip-coating the fabric into a liquid photoresist to ensure application of the photoresist to all parts of the fabric by immersion.

Next, the fabric is exposed to a suitable image pattern of ultraviolet light from the phototool. This image is developed. The unrequited metal is then progressively etched away. Then, the photoresist is removed to leave the required metallic track shape for the heater element, as shown in FIG. 4. The heater element is then cut to the required shape.

The heater element is fixed to a suitable skin or wound contact layer. Suitable materials will be known to the person skilled in the art. The fixing of the heater element is by the interposition of a thermoplastic web between the heater element and the skin or wound contact layer.

A suitable thermoplastic web material is the melt-spun interlining material Vilene (registered trade mark) U25 supplied by Freudenberg Nonwovens Interlining Division (part of Freudenberg Vliesstoffe KG). The U25 grade is made from 100% polyamide and has a random web structure and a weight of 25 grams per square metre. The material softens and fuses when heat is applied at about 130° C. for about 10 seconds with a pressure of 15-30 N/cm$^2$. The web has a high degree of open porosity and so allows the lamination between the skin or wound contact layer and the heater element to give rise to a breathable structure.

Although not shown in FIG. 4, it is preferred that the heater element has a fully flexible tail portion extending away from the main part of the heater element, the tail portion carrying the connection tracks for the heater element (these connection tracks having lower resistance to the heat-generation tracks of the heater element) to terminals formed at the end of the tail portion. In this way, a power supply can be connected to the terminals without disturbing the dressing or pad.

A suitable power supply (not shown) is supplied by Mpower Batteries Limited, consisting of 2×3.6 V lithium ion batteries. Suitable control circuitry is also available from the same source. See also the control circuitry disclosed in WO 03/039417.

Microencapsulated drugs (not shown) are incorporated into the skin contact layer 15 or into the wound contact layer 16. The microcapsules used are of the type that release their contents due to heat activation, e.g. due to melting of the capsule wall material or thermal degradation of the capsule wall material or diffusion of the content of the capsule through the wall due to increased temperature. In particular, microcapsules that gradually release their content on heating are preferred.

In a preferred embodiment, microencapsulated ibuprofen is used, such as is disclosed in the following documents: Adeyeye, C. M., and Price, J. C., "Development and Evaluation of Sustained Release Ibuprofen-Wax Microspheres: I. Effect of Formulation Variables on Physical Characteristics" (Pharmaceutical Research, 8, #11, 1377-1383 (1991) November); Adeyeye, C. M., and Price, J. C., "Development and Evaluation of Sustained Release Ibuprofen-Wax Microspheres: II. In Vitro Dissolution Studies" (Pharmaceutical Research, 11, #4, 575-579 (1994)); Adeyeye, C. M., and J. C. Price, "Chemical, dissolution stability and microscopic evaluation of suspensions of ibuprofen and sustained release ibuprofen-wax microspheres" (Journal of Microencapsulation, 14, (1997)).

In another embodiment, the invention has particular application to assisting in venipuncture and IV cannulation, particularly for paediatric patients.

Venipuncture for laboratory tests and intravenous (IV) insertion are common medical procedures, and many children with chronic illness have these procedures repeatedly performed during the course of their treatment. Needle insertion is the most frightening and bothersome medical procedure for children. Studies have shown that children's previous distress during medical procedures is a predicator of future distress. Some children develop needle phobia that is extremely difficult to treat.

Topical anaesthesia creams have been developed to minimize the discomfort of venipuncture and many children's hospitals have adopted the use of eutectic mixture of lidocaine and prilocalne (EMLA) as part of their pain management standard of practice. Numerous studies have shown that EMLA decreases pain sensation for children during needle sticks (see, for example, Robieux I., Kumar R., Radhakrishnan S., Koren G., "Assessing pain and analgesia with a lidocaine-prilocalne emulsion in infants and toddlers during venipuncture" (J. Pediatr. 1992; 118: 971-973). It has been found that the anaesthetic is more effective for simple venipuncture than for IV cannulation.

EMLA cream (lidocaine 2.5% and prilocalne 2.5%) is an emulsion in which the oil phase is a eutectic mixture of lidocaine and prilocalne in a ratio of 1:1 by weight. This eutectic mixture has a melting point below room temperature and therefore both local anaesthetics exist as a liquid oil rather than as crystals. EMLA is available as a cream but also incorporated into an occlusive dressing having a laminate backing, an absorbent cellulose disc, and an adhesive tape ring.

In use, the EMLA cream is applied liberally to the skin of the back of the hand. An occlusive dressing is then applied to push the cream against the skin and to prevent the cream from leaking away from the required area. The cream must be left in place for between 30 minutes and 1 hour to have the desired anaesthetic effect.

It is found that EMLA may constrict the veins under the skin where it is applied. This makes IV cannulation more difficult.

Incorporation of the heater element into the dressing or pad allows the dressing or pad to be heated to help to vasodilate the veins of interest. Accordingly, the heater element is of assistance in overcoming at least one drawback of using EMLA.

Furthermore, the incorporation of the heater element into the dressing or pad allows the heat generated by the heater element to encourage the deeper and faster transfer of drug into the skin of the patient. This allows a suitable local anaesthetic effect to be achieved more completely and more fully in a faster time. This is of direct use in paediatric medicine, as mentioned above, due to the difficulty that can be encountered with the slow effects of EMLA in normal operation.

The embodiments above have been described by way of example. Modifications of these embodiments, further embodiments and modifications thereof will be apparent to the skilled person on reading this disclosure and as such are within the scope of the invention.

The invention claimed is:

1. A topical application device for topical application for therapeutic treatment, comprising:
   a metallised substrate of porous fabric having a plurality of components each encapsulated with metal wherein the metal on the metallised substrate of fabric is photochemically etched to form a breathable therapeutic heater element by selectively etching out metal encapsulated about the plurality of components of the substrate of porous metallised fabric.

2. A topical application device according to claim 1, further comprising:
   at least one therapeutic agent for delivery to a subject.

3. A topical application device according to claim 2 wherein the delivery of the at least one therapeutic agent to the subject is assisted by operation of the heater element to generate heat.

4. A topical application device according to claim 3 wherein the at least one therapeutic agent are microencapsulated.

5. A topical application device according to claim 4 wherein the at least one therapeutic agent are microencapsulated in microcapsules that melt at a particular initiation temperature to release their contents.

6. A topical application device according to claim 4 wherein the at least one therapeutic agent or are microencapsulated in microcapsules that allow diffusion of the therapeutic agent or agents through their walls.

7. The topical application device according to claim 1 wherein the components of the substrate of porous metallised fabric are individual fibres, the individual fibres being encapsulated in metal prior to the manufacture of the substrate of porous metallised fabric.

8. The topical application device according to claim 1 wherein the components of the substrate of porous metallised fabric are individual yarns, the individual yarns being encapsulated in metal after manufacture of a substrate of a porous fabric to form the substrate of porous metallised fabric.

9. The topical application device according to claim 1 wherein the components of the substrate of porous metallised fabric are individual fibres, the individual fibres being encapsulated in metal after manufacture of a substrate of a porous fabric to form the substrate of porous metallised fabric.

10. The topical application device according to claim 1 wherein the components of the substrate of porous metallised fabric are individual yarns, the individual yarns being encapsulated in metal prior to the manufacture of a substrate of a porous fabric to form the substrate of porous metallised fabric.

* * * * *